US010184864B2

(12) United States Patent
Schwind et al.

(10) Patent No.: US 10,184,864 B2
(45) Date of Patent: Jan. 22, 2019

(54) INTELLIGENT AUTOMATED LOAD CONTROL SYSTEM AND METHOD

(71) Applicants: Brian E. Schwind, Waller, TX (US); Daniel Purvis, Waller, TX (US); Albert Lin, Waller, TX (US)

(72) Inventors: Brian E. Schwind, Waller, TX (US); Daniel Purvis, Waller, TX (US); Albert Lin, Waller, TX (US)

(73) Assignee: MECHANICAL TESTING SERVICES, LLC, Waller, TX (US)

( * ) Notice: Subject to any disclaimer, the term of this patent is extended or adjusted under 35 U.S.C. 154(b) by 0 days.

(21) Appl. No.: 15/367,373

(22) Filed: Dec. 2, 2016

(65) Prior Publication Data

US 2017/0167959 A1 Jun. 15, 2017

Related U.S. Application Data

(60) Provisional application No. 62/265,721, filed on Dec. 10, 2015.

(51) Int. Cl.
*G01N 3/00* (2006.01)
*G01N 3/02* (2006.01)
*G01L 1/26* (2006.01)

(52) U.S. Cl.
CPC .................. *G01N 3/02* (2013.01); *G01L 1/26* (2013.01); *G01N 2203/0202* (2013.01)

(58) Field of Classification Search
CPC ..... G01N 3/02; G01N 2203/0202; G01L 1/26
USPC .......................................................... 73/788
See application file for complete search history.

(56) References Cited

U.S. PATENT DOCUMENTS

| 6,840,082 | B2 * | 1/2005 | Evans | G01N 19/02 73/10 |
| 2003/0101793 | A1 | 6/2003 | Evans | |
| 2005/0217388 | A1 | 10/2005 | Heyman et al. | |
| 2010/0229652 | A1 * | 9/2010 | Jeppesen | G01N 3/08 73/856 |
| 2013/0047741 | A1 * | 2/2013 | Woo | G01N 3/20 73/760 |
| 2015/0073601 | A1 | 3/2015 | Gunness et al. | |

(Continued)

FOREIGN PATENT DOCUMENTS

WO 2014073759 A1 5/2014

OTHER PUBLICATIONS

PCT Application No. PCT/US2016/064894 International Search Report and Written Opinion, ISAKR, dated Apr. 4, 2017.

*Primary Examiner* — Max Noori

(57) ABSTRACT

A system for automating load conditions on a test specimen includes a test equipment assembly that includes one or more test components configured to apply load to the test specimen. The system includes a control system to actuate the load, and includes a controller that receives and transmits data to sensors and actuators operatively connected to the test equipment assembly. The system includes a data analyzer connected to the control system to transmit a loading sequence to the controller for actuating the test equipment assembly. The data analyzer receives and processes the data from the controller to determine whether the test specimen is within an acceptable stress range as the test equipment assembly performs the loading sequence, and transmits data to the controller to reduce the load on the test specimen if the acceptable stress range is exceeded.

19 Claims, 7 Drawing Sheets

(56) References Cited

U.S. PATENT DOCUMENTS

2016/0231210 A1* 8/2016 Ganser ............... G01N 3/36
2017/0138827 A1* 5/2017 Mourad ............... G01N 3/02

* cited by examiner

INTELLIGENT AUTOMATED LOAD CONTROL SYSTEM AND METHOD

CROSS-REFERENCE TO RELATED APPLICATIONS

This application claims the benefit of U.S. Provisional Patent Application having Ser. No. 62/265,721, which was filed Dec. 10, 2015. This priority application is hereby incorporated by reference in its entirety into the present application to the extent consistent with the present application.

BACKGROUND

Quality assurance tests are conducted on equipment used in many industries, including the automotive industry, heating, ventilation, and air conditioning ("HVAC") industry, medical industry, environmental industry, and process industry. For example, quality assurance tests may be conducted on equipment to verify the equipment will not fail when exposed to one or more types of load conditions, such as elevated internal pressure, tension loading, compression loading, or bending load. When testing equipment to the edge of performance, it is desirable to have state of the art load control.

A common method used to test equipment includes using a control system to automate a preset load sequence on the equipment. The control system will direct a test assembly to apply loads to the equipment in timed intervals. The control system may further record the loads applied to the equipment and may monitor any changes in the equipment, such as internal pressure, deflection, etc. In addition, during the load sequence, or separate from the load sequence, an operator may be allowed to manually control a test parameter, such as adjusting pressure or tension applied to the equipment. In some instances, the control system may be equipped to terminate the load sequence if any preset condition is exceeded, in order to avoid equipment failure.

However, this method of testing may result in equipment failure in certain circumstances. For example, while altering one test parameter, other control parameters could become unstable, resulting in equipment failure. Alternatively, while testing equipment required to withstand certain loads for a specified duration, if one preset condition is exceeded, the control system may completely terminate the load sequence resulting in a failed test.

What is needed, then, is a system and method for controlling load sequences applied to equipment that addresses the issues discussed above.

SUMMARY

In one embodiment, a system for automating load conditions on a test specimen may include a test equipment assembly configured to apply one or more loads to the test specimen, wherein the test equipment assembly includes one or more test components. The system may also include a control system operatively connected to the test equipment assembly. The control system may be configured to actuate the one or more loads applied to the test specimen. The control system may include a controller configured to receive and transmit data, a plurality of sensors operatively connected to the test equipment assembly and configured to transmit real time data related to the test equipment assembly or the test specimen to the controller, and a plurality of actuators operatively connected to the test equipment assembly and configured to actuate the one or more test components via the data transmitted from the controller. The system for automating load conditions on a test specimen may also include a data analyzer operatively connected to the control system and configured to transmit a loading sequence to the controller for actuating the test equipment assembly, receive and process the data from the controller to determine whether the test specimen is within an acceptable stress range as the test equipment assembly performs the loading sequence, and transmit data to the controller to reduce the one or more loads on the test specimen if the acceptable stress range is exceeded.

In one embodiment, a system for automating load conditions on a test specimen may include a test equipment assembly configured to apply a load to the test specimen, and a control system operatively connected to the test equipment assembly. The control system may include an actuator operatively connected to the test equipment assembly and configured to actuate the test equipment assembly to apply the load to the test specimen. The control system may also include a controller configured to transmit data to the actuator to apply the load to the test specimen and to receive data related to the load applied to the test specimen. The system may further include a data analyzer operatively connected to the control system, which may be configured to operate in conjunction with the controller. The data analyzer may calculate multiple types of stress on the test specimen based on the load applied to the test specimen, determine whether one or more of the multiple types of stress exceeds an acceptable limit, and transmit data to the controller directing the controller to adjust the applied load if the one or more of the multiple types of stress exceeds the acceptable limit.

In one embodiment, a method for automating load conditions on a test specimen may include positioning the test specimen within a test equipment assembly. The test equipment assembly may include one or more test components configured to apply a load to the test specimen. The method may also include operatively connecting one or more actuators of a control system to the one or more test components. The control system may be operatively connected to a data analyzer and configured to operate in conjunction with the data analyzer. The method may include inputting a loading sequence into the data analyzer. The loading sequence may direct the one or more actuators to apply the load to the test specimen in timed intervals. The method may also include transmitting the loading sequence to the control system, whereby the control system is configured to actuate the one or more actuators according to the loading sequence. Further, the method may also include gathering real time data related to the load applied to the test specimen via the control system, transmitting the real time data to the data analyzer, calculating stress of the test specimen based on the real time data and the load being applied to the test specimen via the loading sequence, and adjusting the loading sequence if the stress of the test specimen exceeds an acceptable limit.

BRIEF DESCRIPTION OF THE DRAWINGS

The present disclosure is best understood from the following detailed description when read with the accompanying Figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
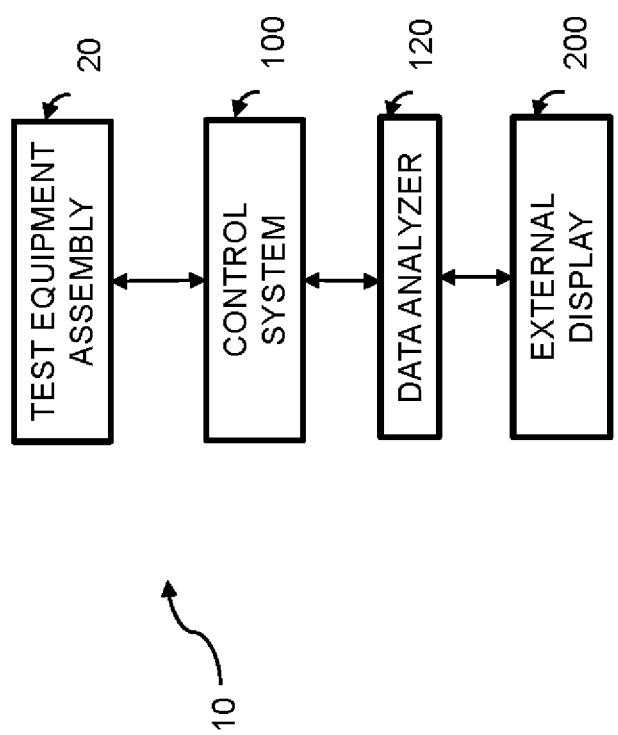
FIG. 1 is a block diagram of a system for automating load conditions on a test specimen, according to one or more embodiments disclosed.

It is to be understood that the following disclosure describes several exemplary embodiments for implementing different features, structures, or functions of the invention. Exemplary embodiments of components, arrangements, and configurations are described below to simplify the present disclosure; however, these exemplary embodiments are provided merely as examples and are not intended to limit the scope of the invention. Additionally, the present disclosure may repeat reference numerals and/or letters in the various exemplary embodiments and across the Figures provided herein. This repetition is for the purpose of simplicity and clarity and does not in itself dictate a relationship between the various exemplary embodiments and/or configurations discussed in the various Figures. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Finally, the exemplary embodiments presented below may be combined in any combination of ways, i.e., any element from one exemplary embodiment may be used in any other exemplary embodiment, without departing from the scope of the disclosure.

Additionally, certain terms are used throughout the following description and claims to refer to particular components. As one skilled in the art will appreciate, various entities may refer to the same component by different names, and as such, the naming convention for the elements described herein is not intended to limit the scope of the invention, unless otherwise specifically defined herein. Further, the naming convention used herein is not intended to distinguish between components that differ in name but not function. Additionally, in the following discussion and in the claims, the terms "including" and "comprising" are used in an open-ended fashion, and thus should be interpreted to mean "including, but not limited to." All numerical values in this disclosure may be exact or approximate values unless otherwise specifically stated. Accordingly, various embodiments of the disclosure may deviate from the numbers, values, and ranges disclosed herein without departing from the intended scope. Furthermore, as it is used in the claims or specification, the term "or" is intended to encompass both exclusive and inclusive cases, i.e., "A or B" is intended to be synonymous with "at least one of A and B," unless otherwise expressly specified herein.

FIG. 1 illustrates a block diagram of a system 10 for automating load conditions on a test specimen 15 (shown in FIG. 2), according to one or more embodiments disclosed. As will be described in more detail herein, the system 10 may include a test equipment assembly 20 configured to apply various loads to the test specimen 15 in timed intervals. The system 10 may include a control system 100 operatively connected to the test equipment assembly 20 and configured to receive information about the load conditions applied to the test specimen 15 by the test equipment assembly 20. The control system 100 may also receive data such as measurements relative to real time conditions on the test specimen 15 (e.g. actual pressure, actual deflection, etc.). The control system 100 may be further configured to automatically adjust, shut-down, or otherwise control the loads applied to the test specimen 15 by the test equipment assembly 20. The system 10 may further include a data analyzer 120 operatively connected to the control system 100 and configured to receive and analyze the data received by the control system 100. The data analyzer 120 may be configured to operate in conjunction with the control system 100 to adjust or terminate the loads applied by the test equipment assembly 20 based on pre-set conditions that indicate the test specimen 15 may fail. The system 10 may also include an external display 200 operatively connected to the data analyzer 120 and configured to display the various loads being applied to the test specimen 15 and/or various stresses of the test specimen 15. Based on the information shown on the external display 200, an operator may manually adjust or control the loads applied to the test specimen 15.

Figure 2:
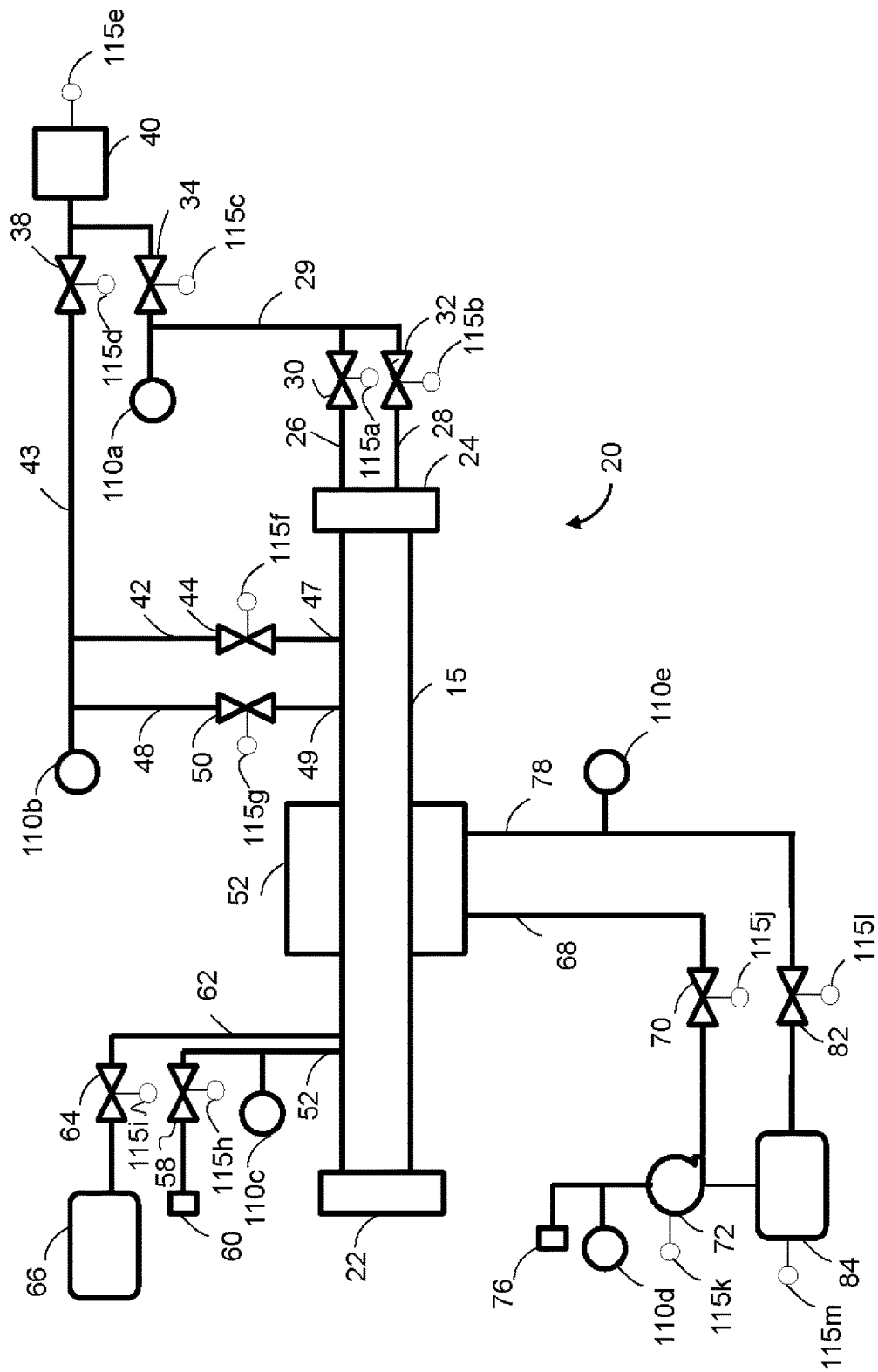
FIG. 2 illustrates a schematic of the test equipment assembly that may be included in the system shown in FIG. 1, according to one or more embodiments disclosed.

FIG. 2 illustrates a schematic of the test equipment assembly 20 that may be included in the system 10 for automating load conditions on the test specimen 15, according to one or more embodiments disclosed. The test specimen 15 may include one or more tubular sections, such as joints of pipe, liner hangers, or packers. However, a wide variety of test specimens 15 is contemplated for use with the system 10.

In one embodiment, the test equipment assembly 20 may include a first test element 22 and a second test element 24, which may be positioned at a first axial end and a second axial end of the test specimen 15, respectively. In one embodiment, the first and second test elements 22, 24 may be a crosshead or a torsional jig operatively connected to a piston that may be hydraulically actuated. In one embodiment, the first and/or second test element 22, 24 may be configured to apply tension or compression loading to the test specimen 15. The first or second test element 22, 24 may also be configured to apply torsional loading to the test specimen 15. The first and second test elements 22, 24 may be connected to the test specimen 15 via components such as fittings. The fittings may include flanges or boot connections, although other fittings are contemplated. The test elements 22, 24 may be connected to the test specimen 15 such that the test elements 22, 24 may be configured to contain pressure within the test specimen 15.

For example, as shown in FIG. 2, the second test element 24 may include a hydraulic system that is configured to apply axial tension or compression loads to the test specimen 15. The hydraulic system may include a high pressure unit 40 configured to inject a fluid, such as air, into a conduit 29 at an elevated pressure. A valve 34 may control the amount of fluid flowing through the conduit 29. The fluid may flow through the conduit 29 and into an inlet conduit 26 and actuate the second test element 24, applying a compression load to the test specimen 15. A valve 30 may prohibit fluid from entering or leaving the conduit 26. The fluid in the second test element 24, and the pressure contained therein, may be released by opening a valve 32. When the valve 32 is opened, fluid may move through and from an outlet conduit 28 and into the conduit 29. Alternatively, the high pressure unit 40 may be configured to draw fluid, such as air, from the second test element 24 into the outlet conduit 28, and further into the conduit 29, thereby moving the second test element 24 away from the first test element 22 and applying an axial load to the test specimen 15.

In one embodiment, the test equipment assembly 20 may be configured to apply bending loads to the test specimen at one or more locations along an axis of the test specimen 15. The high pressure unit 40 may be configured to inject fluid into a conduit 43 when a valve 38 is open. After fluid flows through the conduit 43, the fluid may enter inlet conduits 42 and 48, and may thereby flow through valves 44 and 50, such that the test equipment assembly 20 may be configured to apply load to one or more bend points 47 and 49, respectively. Further, either valve 44 or valve 50 may be closed to position all load on a single bend point, such as bend point 47 or bend point 49, or either valve 44 or valve 50 may be partially opened such that the bend points 47 and 49 receive a different amount of load.

In one embodiment, the test specimen 15 may be pressurized internally as a loading condition. As shown in FIG. 2, a fluid vessel 66 may inject a fluid, such as nitrogen, into the test specimen 15 via an injection conduit 62. A valve 64 may be configured to control the amount of fluid flowing into the test specimen 15, and may prevent fluid from flowing through the conduit 62. A venting conduit 52 may be configured to remove fluid from the test specimen 15. Fluid may flow through a valve 58 and to the atmosphere via a vent 60. The valve 58 may control the amount of fluid vented to the atmosphere or prevent fluid from venting to the atmosphere.

In one embodiment, the test specimen 15 may be heated or cooled as a loading condition. A vessel 84 may store a fluid such as oil, and the vessel 84 may be configured to preheat or precool the fluid via a heat exchanger fluidly connected to the vessel 84. In one embodiment, the vessel 84 may be or include the heat exchanger. A pump 72 may be configured to draw the fluid from the vessel 84, and may circulate the fluid through a conduit 68 and into a sleeve 52 that surrounds at least a portion of the test specimen 15. As the heated or cooled fluid enters the sleeve 52, the heated or cooled fluid also surrounds the portion of the test specimen 15, and in turn, heats or cools the test specimen 15. In addition, an air vent 76 may be operatively connected to the pump 72 to relieve excess pressure in the pump 72. In one embodiment, a valve 70 may be configured to control the amount of fluid flowing into the sleeve 52 or may prevent fluid from flowing into the sleeve 52. A conduit 78 may be configured to transfer fluid from the sleeve 52 to the vessel 84. Further, a valve 82 may control the amount of fluid flowing out of the sleeve 52 or may prevent fluid from returning to the vessel 84.

Figure 3:
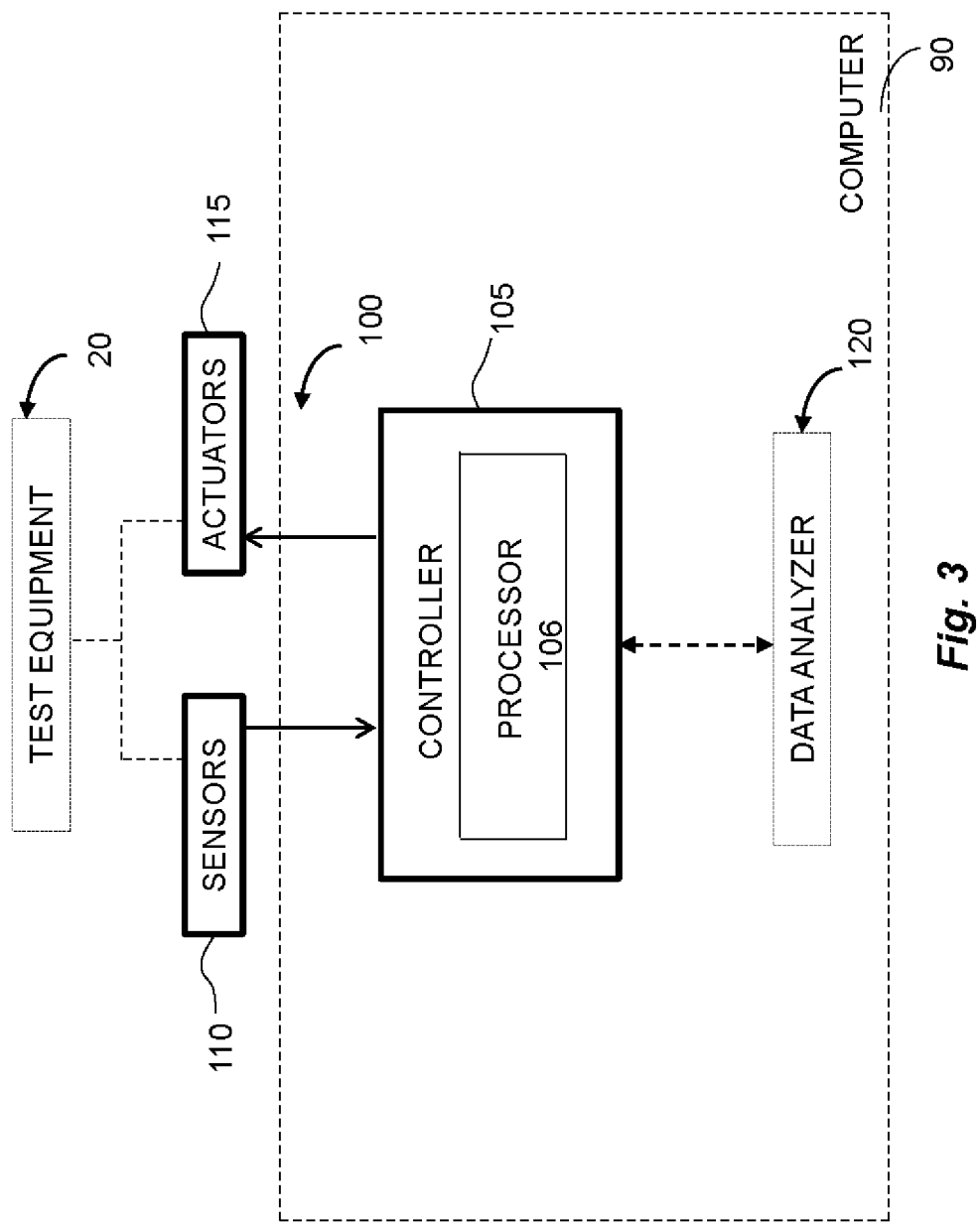
FIG. 3 illustrates a block diagram of a controller that may be included in the system of FIG. 1, according to one or more embodiments disclosed.

FIG. 3 illustrates a block diagram for the control system 100 that may be included in the system 10 for automating load conditions on the test specimen 15, according to one or more embodiments disclosed. The control system 100 may include a controller 105, which may be configured to communicate with the test equipment assembly 20 and the data analyzer 120 (as shown in FIG. 1). The controller 105 may include a processor 106 that may be configured to process or store data to and from the test equipment assembly 20 and may be configured to process or store data to and from the data analyzer 120. In one embodiment, the processor 106 may be or include a floating-point processor, which may reduce or eliminate data overflow errors and may reduce inaccuracies related to the data caused by unnecessary rounding. In one embodiment, the floating-point processor may be a CompactRIO® processor produced by National Instruments Corporation of Austin, Tex.

The control system 100 may also include a plurality of sensors 110a-e, as shown in FIG. 2. The sensors 110a-e may be operatively connected to the test equipment assembly 20 and configured to read real time measurements of load conditions (e.g. sensor data) within the test equipment assembly 20 and the test specimen 15 during a load test. For example, the sensor data may include deflection measurements, temperature, pressure, or flow rate information. In turn, the sensors 110a-e may be configured to output the sensor data to the controller 105. The sensors 110a-e may be configured to transmit the sensor data via a wired or wireless connection to the controller 105. In one embodiment, the controller 105 may process the sensor data by filtering, calibrating, or scaling the sensor data. In one embodiment, the controller 105 may also be configured to perform higher level built-in analysis functions related to the sensor data such as generating statistics, transforming the data, detecting peaks, constructing data lookup tables, and/or generating signals.

The control system 100 may also include a plurality of actuators 115a-m, as shown in FIG. 2. The controller 105 of the control system 100 may be configured to communicate with the actuators 115a-m and may be configured to actuate the test components of the test equipment assembly 20. Once one or more of the actuators 115a-m are actuated, the test equipment assembly 20 may apply a load to the test specimen 15.

The actuators 115a-m may be operatively connected to one or more test components of the test equipment assembly 20. As used herein, the test components refer to any component of the test equipment assembly 20 that operatively controls or applies load to the test specimen 15. For example, some of the actuators 115a-m, such as the actuators 115a-d, f-j and l, may be operatively connected to the valves 30, 32, 34, 38, 44, 50, 58, 64, 70, and 82, respectively, and may be configured to control the opening and closing of the valves 30, 32, 34, 38, 44, 50, 58, 64, 70, and 82. In another example, some of the actuators 115a-m, such as the actuators 115e, k, and m, may be operatively connected to the HPU 40, the fluid vessel 66, or the vessel 84, respectively, and may be configured to turn the test components on and off, adjust pressure, adjust temperature, and/or make other adjustments to the test components. The actuators 115a-m may be configured to communicate with the controller 105 via a wired or wireless connection.

As shown in FIGS. 1 and 3, the system 10 may also include a data analyzer 120, which may be operatively connected to the control system 100. The data analyzer 120 may be configured to operate in conjunction with the control system 100. The data analyzer 120 may include software that may run or create code using a computer 90, such as a personal computer, an embedded controller, an FPGA chip, or handheld Personal Digital Assistant ("PDA"). In one embodiment, the software may comprise LabVIEW®, which is produced by National Instruments Corporation of Austin, Tex. In one embodiment, the software may include LabVIEW® Real-Time or LabVIEW® Field-programmable Gate Array ("FPGA").

Figure 4:
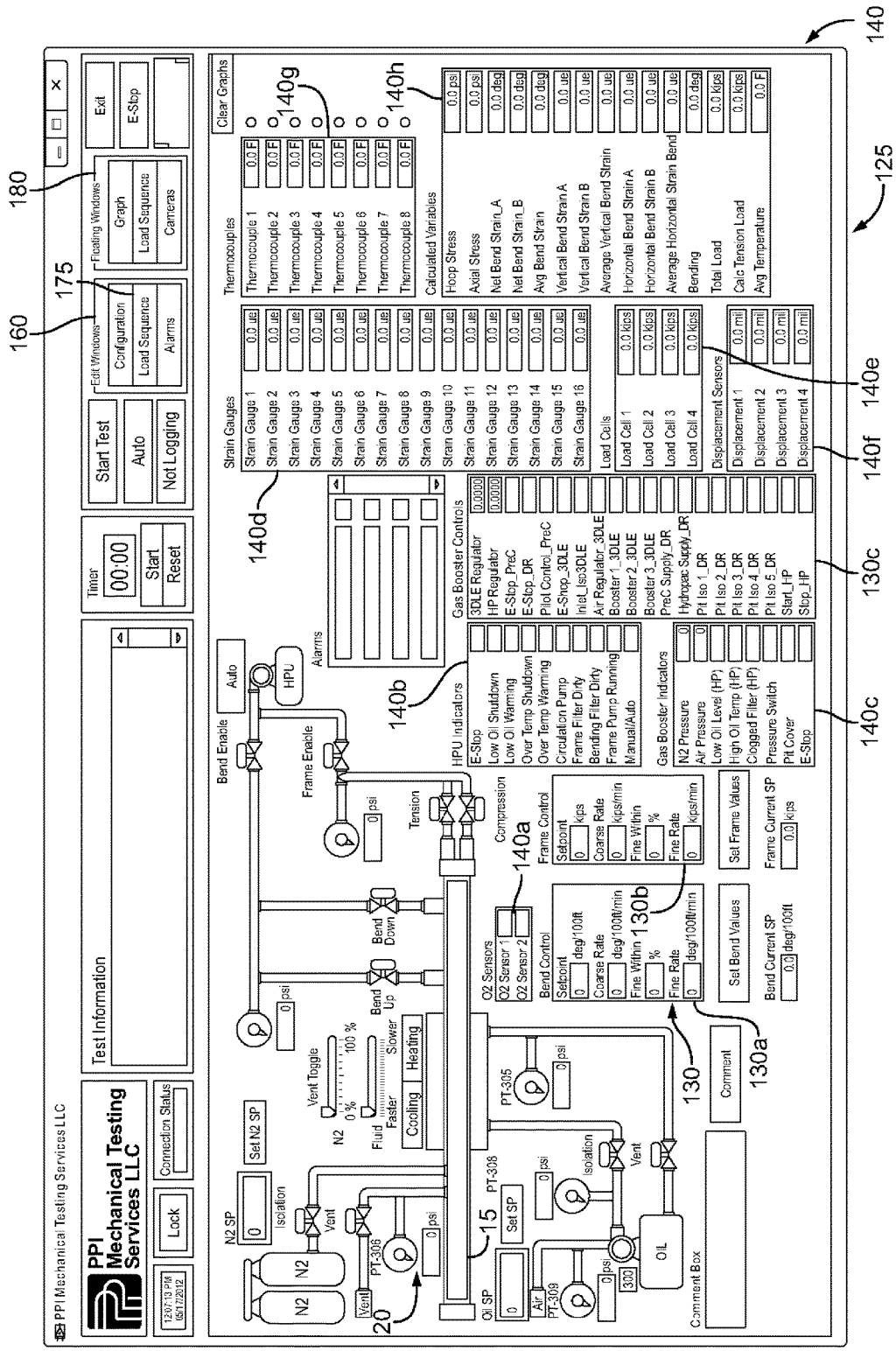
FIG. 4 illustrates a graphical user interface of a data analyzer that may be included in the system of FIG. 1, according to one or more embodiments disclosed.

FIG. 4 is one embodiment of an exemplary graphical user interface ("GUI") 125 to be used with the system 10 for automating load conditions on a test specimen 15. The GUI 125 may be displayed on the external display 200, which may be operatively connected to the data analyzer 120, as indicated in FIG. 1. The data analyzer 120 may be configured to support networking communication standards such as TCP/IP, UDP, OPC, Active X, and others that may be used to transmit data to the GUI 125. Further, the data analyzer 120 may be configured to support such networking communication standards to transmit data to the control system 100.

As shown in FIG. 4, the GUI 125 may include a diagram of the test equipment assembly 20 and the test specimen 15, similar to that shown in FIG. 2. The GUI 125 may also include one or more user controls 130a-c, such as bend controls 130a, frame controls 130b, and gas booster controls 130c. The controls 130a-c may be configured so that a user may manually alter the loads during an active load test. For example, a user may modify a load input via one or more of the user controls 130a-c in the GUI 125. Once the one or more user controls 130a-c are modified, the data analyzer 120 may transmit data to the controller 105 directing such modification, and the controller 105 may then transmit a command or data to the appropriate actuator(s) 115a-m in the test equipment assembly 20 to complete such load modification. The GUI 125 may also include one or more indicators 140a-h, such as oxygen sensor indicators 140a, high pressure unit ("HPU") indicators 140b, gas booster indicators 140c, strain gauge indicators 140d, load cell indicators 140e, displacement sensor indicators 140f, thermocouple indicators 140g, and calculated variables indicators 140h. The indicators 140a-h may be configured to provide the real time measurements that are transmitted from the sensors 110a-e to the controller 105. The controller 105 transmits the data to the data analyzer 120, which may then display the information via the indicators 140a-h shown on the GUI 125.

Figure 5:
FIG. 5 illustrates another graphical user interface of a data analyzer that may be included in the system of FIG. 1, according to one or more embodiments disclosed.

In one embodiment, the data analyzer 120 may include a plurality of GUIs 125. The plurality of GUIs 125 may be configured to switch between the GUIs 125 by user icons, such as a configuration icon 160, a load sequence icon 175, or a graph icon 180, as shown in the GUI 125 in FIG. 4. For example, one GUI 125 may include a specification screen 165, as shown in FIG. 5, which may be accessed by selecting the configuration icon 160 (shown in FIG. 4). The specification screen 165 may be configured for a user to input specifications related to the test specimen 15. For example, in FIG. 5, the specification screen 165 may be configured so that a user may input an outside diameter 166 of the test specimen 15, a wall thickness 168 of the test specimen 15, an internal diameter 170 of the test specimen 15, a yield strength 172 of the test specimen 15, and a logging interval 174. The data analyzer 120 may be configured to take the specifications of the test specimen 15 and calculate or otherwise determine theoretical stress limits of the test specimen 15. In one embodiment, the data analyzer 120 may also be configured to calculate or otherwise determine maximum allowable stress limits, or acceptable stress limits, of the test specimen 15 during a load test. For example, the data analyzer 120 may be configured to define and calculate acceptable stress limits of the test specimen 15 as 80% of the theoretical stress limits of the test specimen 15.

Another GUI 125 may include a load sequence screen (not shown). The load sequence screen may be configured so that a user may upload a preferred load sequence for the test specimen 15 to the data analyzer 120, which would, in turn, transmit instructions, or data, to the controller 105 for automating the load test. The load sequence may include a plurality of loads to be applied to the test specimen 15 over timed intervals by certain test components of the test equipment assembly 20.

Figure 6:
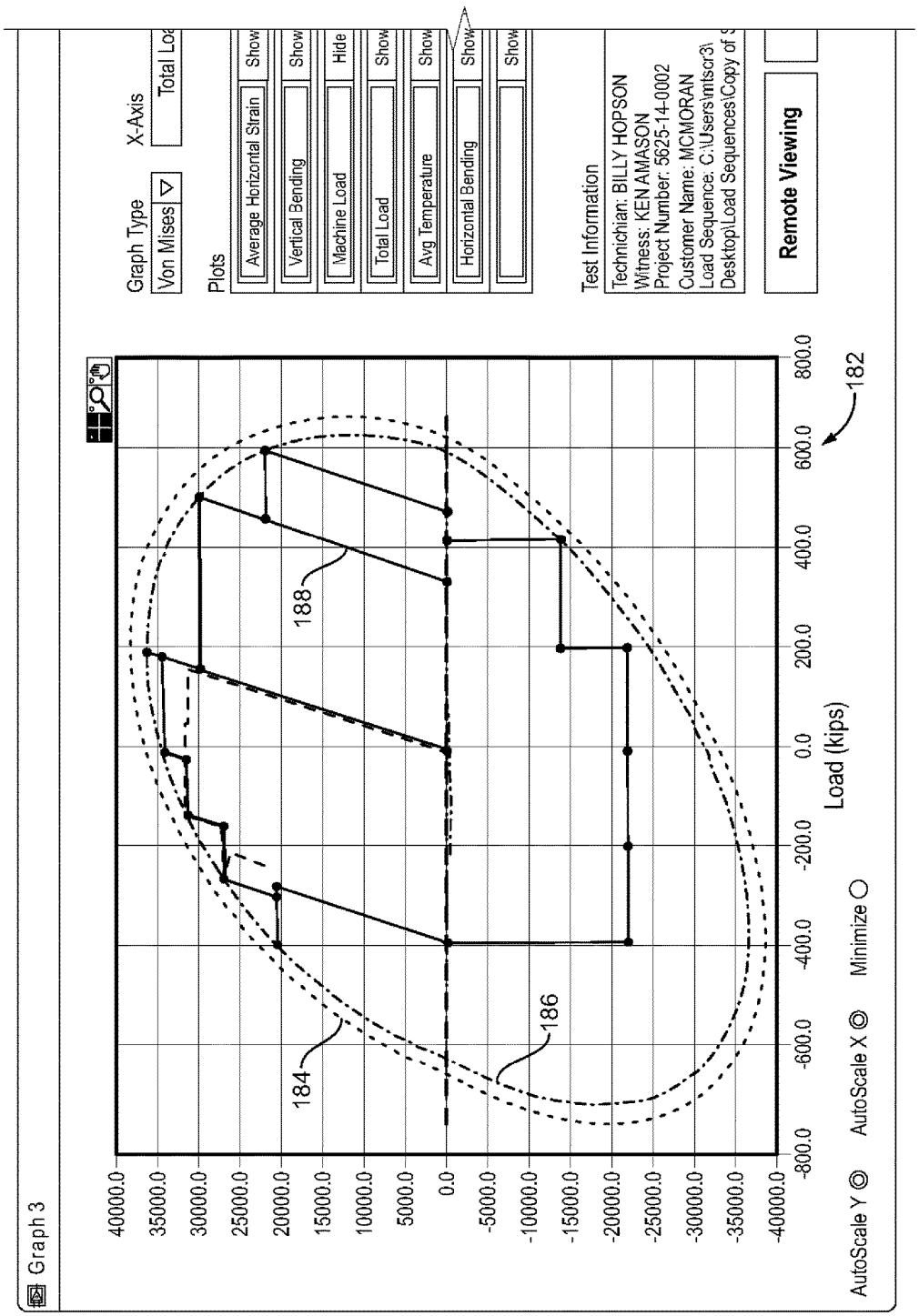
FIG. 6 illustrates another graphical user interface of a data analyzer that may be included in the system of FIG. 1, according to one or more embodiments disclosed.

During the load test of the test specimen 15, a user may select a graph icon 180, as shown in FIG. 4. The graph icon 180 may direct the data analyzer 120 to show another GUI 125 on the external display 200, which may include a graph screen 182. In one embodiment, the graph screen 182 may show a Von Mises graph of the test specimen 15, as seen in FIG. 6. In one embodiment, the graph screen 182 may include a theoretical limit ellipse 184, which illustrates the theoretical stress limits of the test specimen 15. The graph screen 182 may also include a testing range ellipse 186, which illustrates the maximum allowable stress limits, or acceptable stress limits, of the test specimen 15.

As discussed previously, in one embodiment, the data analyzer 120 may calculate or otherwise determine the theoretical stress limits or maximum allowable stress limits of the test specimen 15. The graph screen 182 may also include a linear depiction of the actual stresses 188 of the test specimen 15 as the load sequence is applied to the test specimen 15 during the load test. The Von Mises graph may graphically show whether the load sequence is within the test parameters of the test specimen 15 if the linear depiction of the actual stresses 188 falls within the testing range ellipse 186. If the actual stresses 188 of the test specimen 105 move beyond the specified testing range, as graphically illustrated by moving outside of the testing range ellipse 186 in FIG. 6, an alarm may sound and the data analyzer 120 may automatically transmit data to the controller 105 to either adjust one or more loads or shut down the test. Such automatic adjustment or shut down may prevent catastrophic failure of the test specimen 15 during a load test. Further, automatic adjustments of one or more loads, as opposed to shut down, will prevent a load test from reaching inconclusive results.

Figure 7:
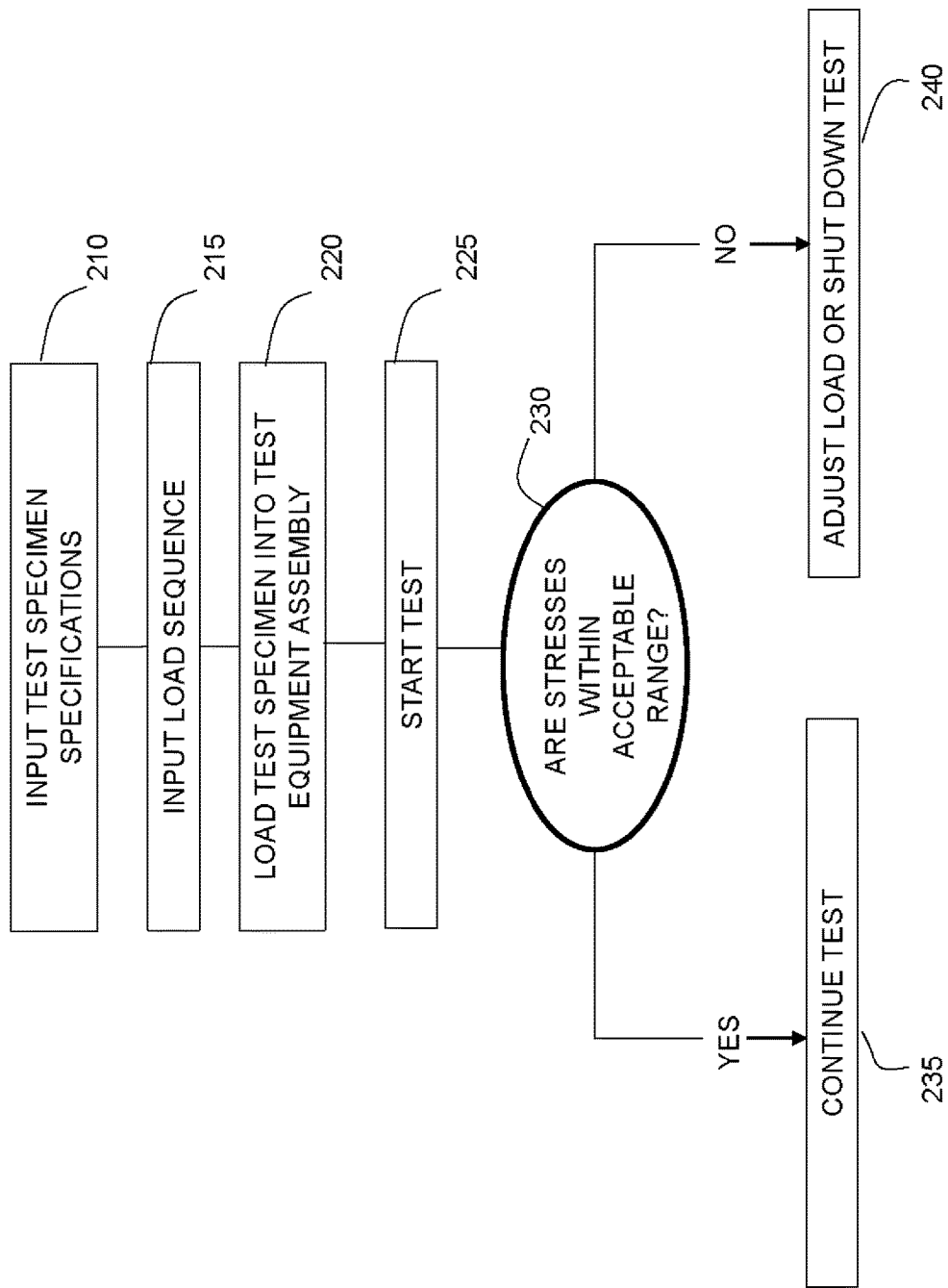
FIG. 7 is a flowchart of an illustrative method for automating load conditions on a test specimen, according to one or more embodiments disclosed.

Turning now to FIG. 7, with continued reference to FIGS. 1-6, a flowchart is provided of an illustrative method for automating load conditions on a test specimen 15, according to one or more embodiments disclosed. Specifications of the test specimen 15 may be input into the system 10 for automating load conditions on the test specimen 15, as at 210. As discussed previously, the specifications may be input into the data analyzer 120 via a GUI 125 such as the one shown in FIG. 5. In one embodiment, a load sequence may be input into the system 10, as at 215. For example, the load sequence may be input into the data analyzer 120, which may be transmitted to the control system 100 for actuating the test equipment assembly 20. The test specimen 15 may be loaded into the test equipment assembly 20, as at 220. In one embodiment, the test may begin as the load sequence is transmitted from the control system 100 to one or more of the actuators 115a-m connected to the test equipment assembly 20, as at 225. During the test, the control system 100 may receive and monitor real time measurements of one or more sensors 110a-e positioned on the test equipment assembly 20 and the test specimen 15. The system 10 may determine whether the real time measurements indicate that the test specimen 15 is within an acceptable stress range, as at 230. In one embodiment, the acceptable stress range includes the maximum allowable stress limits, or acceptable stress limits, as determined by the data analyzer 120 based on the specifications of the test specimen 15. As discussed previously, the data analyzer 120 may use the specifications of the test specimen 15 and the real time measurements from one or more of the sensors 110a-e to calculate the actual stresses on the test specimen 15. If all of the actual stresses on the test specimen 15 are within an acceptable test range, the test may be continued, as at 235. If one or more of the actual stresses on the test specimen 15 are not within an acceptable test range, the system 10 may adjust one or more loads applied to the test specimen 15, as at 240. Specifically, the data analyzer 120 may calculate a new one or more loads to be applied to the test specimen 15 to maintain an appropriate level of stress on the test specimen 15 during the load test. Alternatively, the data analyzer 120 may shut down the load test.

The foregoing has outlined features of several embodiments so that those skilled in the art may better understand the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

We claim:

1. A system for automating load conditions on a test specimen, comprising:
   a test equipment assembly configured to apply one or more loads to the test specimen, the test equipment assembly including one or more test components;
   a control system operatively connected to the test equipment assembly, the control system configured to actuate the one or more loads applied to the test specimen, the control system comprising:
      a controller configured to receive and transmit data,
      a plurality of sensors operatively connected to the test equipment assembly and configured to transmit real time data related to the test equipment assembly or the test specimen to the controller, and
      a plurality of actuators operatively connected to the test equipment assembly and configured to actuate the one or more test components via the data transmitted from the controller; and
   a data analyzer operatively connected to the control system and configured to calculate a theoretical stress limit of the test specimen based on specifications of the test specimen input into the data analyzer, transmit a loading sequence to the controller for actuating the test equipment assembly, receive and process the data from the controller to determine whether the test specimen is within an acceptable stress range compared to the theoretical stress limit as the test equipment assembly performs the loading sequence, and transmit data to the controller to reduce the one or more loads on the test specimen if the acceptable stress range is exceeded, such that a portion of the one or more loads on the test specimen is maintained and the test specimen is within the acceptable stress range.

2. The system of claim 1, wherein the controller comprises a floating point processor.

3. The system of claim 1, wherein the data analyzer is configured to operate on a computer.

4. The system of claim 3, further comprising an external display operatively connected to the data analyzer.

5. The system of claim 4, wherein the data analyzer comprises one or more graphical user interfaces displayed on the external display, the one or more graphical user interfaces comprising:
   controls configured to allow a user to manually alter the one or more loads during an active load test, and
   indicators configured to provide the real time data transmitted from the plurality of sensors.

6. The system of claim 5, wherein the data analyzer comprises a plurality of graphical user interfaces.

7. The system of claim 6, wherein one graphical user interface of the plurality of graphical user interfaces is configured to display a Von Mises graph comprising a testing range ellipse and a linear depiction of actual stresses exerted on the test specimen during the loading sequence.

8. The system of claim 7, wherein the data analyzer is configured to recalculate the one or more loads applied to the test specimen when the acceptable stress range is exceeded.

9. A system for automating load conditions on a test specimen, comprising:
   a test equipment assembly configured to apply a load to the test specimen;
   a control system operatively connected to the test equipment assembly and comprising:
      an actuator operatively connected to the test equipment assembly and configured to actuate the test equipment assembly to apply the load to the test specimen, and
      a controller configured to transmit data to the actuator to apply the load to the test specimen and to receive data related to the load applied to the test specimen; and
   a data analyzer operatively connected to the control system and configured to:
      operate in conjunction with the controller,
      calculate a theoretical stress limit of the test specimen based on specifications of the test specimen input into the data analyzer,
      calculate multiple types of stress on the test specimen based on the load applied to the test specimen,
      determine whether a stress of the multiple types of stress exceeds an acceptable limit compared to the theoretical stress limit, and
      transmit data to the controller directing the controller to adjust the applied load if the stress of the multiple types of stress exceeds the acceptable limit, such that a portion of the applied load on the test specimen is maintained and the test specimen is within the acceptable limit.

10. The system of claim 9, wherein the data analyzer is configured to upload a loading sequence to transmit to the controller, wherein the loading sequence directs a plurality of loads to be applied to the test specimen at timed intervals.

11. The system of claim 10, further comprising an external display operatively connected to the data analyzer, wherein the data analyzer comprises a graphical user interface displayed on the external display.

12. The system of claim 11, wherein:
   the data analyzer is communicatively coupled to a network, and
   the data analyzer is configured to transmit data to and receive data from the network.

13. The system of claim 10, wherein the controller comprises a floating point processor.

14. The system of claim 13, wherein the controller is configured to receive data related to the load applied to the test specimen from one or more sensors operatively connected to the test equipment assembly or to the test specimen.

15. The system of claim 14, wherein the controller is configured to adjust the plurality of loads if the stress of the multiple types of stress calculated by the data analyzer exceeds the acceptable limit.

16. A method for automating load conditions on a test specimen, comprising:
    positioning the test specimen within a test equipment assembly, the test equipment assembly including one or more test components configured to apply a load to the test specimen;
    operatively connecting one or more actuators of a control system to the one or more test components, the control system operatively connected to a data analyzer and configured to operate in conjunction with the data analyzer;
    inputting specifications of the test specimen into the data analyzer;
    calculating a theoretical stress limit of the test specimen based on the specifications of the test specimen input into the data analyzer;
    inputting a loading sequence into the data analyzer, the loading sequence directing the one or more actuators to apply the load to the test specimen in timed intervals;
    transmitting the loading sequence to the control system, whereby the control system is configured to actuate the one or more actuators according to the loading sequence;
    gathering real time data related to the load applied to the test specimen via the control system;
    transmitting the real time data to the data analyzer;
    calculating stress of the test specimen based on the real time data and the load being applied to the test specimen via the loading sequence; and
    determining if the stress exceeds an acceptable limit compared to the theoretical stress limit;
    adjusting the loading sequence if the stress of the test specimen exceeds an acceptable limit, such that a portion of the load applied to the test specimen is maintained and the test specimen is within the acceptable limit.

17. The method of claim 16, wherein the data analyzer automatically adjusts the loading sequence of the test specimen if the stress of the test specimen exceeds the acceptable limit.

18. The method of claim 17, wherein a plurality of loads are applied to the test specimen in the timed intervals.

19. The method of claim 18, wherein one or more loads of the plurality of loads may be automatically adjusted by the data analyzer if the stress of the test specimen exceeds the acceptable limit.

* * * * *